United States Patent
Sykes

(10) Patent No.: US 10,844,850 B2
(45) Date of Patent: Nov. 24, 2020

(54) PUMP MONITORING SYSTEM

(71) Applicant: Keymed (Medical & Industrial Equipment) Ltd., Southend-on-Sea (GB)

(72) Inventor: Gareth Sykes, Southend-on-Sea (GB)

(73) Assignee: Keymed (Medical & Industrial Equipment) Ltd., Essex (GB)

(*) Notice: Subject to any disclaimer, the term of this patent is extended or adjusted under 35 U.S.C. 154(b) by 9 days.

(21) Appl. No.: 16/352,309

(22) Filed: Mar. 13, 2019

(65) Prior Publication Data

US 2019/0293062 A1  Sep. 26, 2019

(30) Foreign Application Priority Data

Mar. 22, 2018 (GB) .................................. 1804602.9

(51) Int. Cl.
*F04B 43/00* (2006.01)
*F04B 49/06* (2006.01)
*F04B 43/12* (2006.01)
*F04B 51/00* (2006.01)
(Continued)

(52) U.S. Cl.
CPC ..... *F04B 43/0081* (2013.01); *A61M 5/14232* (2013.01); *F04B 43/12* (2013.01);
(Continued)

(58) Field of Classification Search
CPC ...... F04B 43/12; F04B 2207/70; F04B 37/10; F04B 43/0081; F04B 43/1253; F04B 49/02; F04B 49/065; F04B 51/00; F04B 49/06; A61M 2205/3592; A61M 2205/6054; A61M 39/08; A61M 5/14232; B67D 7/20;
(Continued)

(56) References Cited

U.S. PATENT DOCUMENTS

2005/0205658 A1* 9/2005 Baker ................ G06K 7/10079
235/375
2009/0229455 A1 9/2009 Eichner
(Continued)

FOREIGN PATENT DOCUMENTS

DE 102005059566 A1 6/2007
DE 202012009626 U1 10/2013
(Continued)

OTHER PUBLICATIONS

European Patent Office, Extended European Patent Office in European Patent Application No. 19161206.8, 7 pp. (dated Jul. 29, 2019).
(Continued)

*Primary Examiner* — Dominick L Plakkoottam
(74) *Attorney, Agent, or Firm* — Leydig, Voit & Mayer, Ltd.

(57) ABSTRACT

A pump monitoring system includes a pump with a pump body and a releasable head. An RFID transponder is secured to the pump head and an RFID reader in communication with a processor is provided in the pump body. The transponder receives and stores information relating to operation of the pump head. The reader reads information from the transponder and transmits further information to the transponder. The processor interprets the information from the transponder and controls operation of the pump in response.

12 Claims, 1 Drawing Sheet

(51) Int. Cl.
    *A61M 5/142*  (2006.01)
    *G16H 40/40*  (2018.01)
    *F04B 37/10*  (2006.01)
    *F04B 49/02*  (2006.01)

(52) U.S. Cl.
    CPC ........ *F04B 43/1253* (2013.01); *F04B 49/065* (2013.01); *F04B 51/00* (2013.01); *A61M 2205/3592* (2013.01); *F04B 37/10* (2013.01); *F04B 49/02* (2013.01); *F04B 2207/70* (2013.01); *G16H 40/40* (2018.01)

(58) Field of Classification Search
    CPC .............. G06K 7/0008; G06K 7/10336; G06K 7/10366; G16H 40/04
    See application file for complete search history.

(56) References Cited

U.S. PATENT DOCUMENTS

| | | | | |
|---|---|---|---|---|
| 2011/0052423 | A1* | 3/2011 | Gambier | F04B 49/065 417/63 |
| 2012/0027622 | A1* | 2/2012 | Ashburn | A61M 39/08 417/53 |
| 2015/0021356 | A1* | 1/2015 | Witchell | F04B 43/12 222/23 |
| 2016/0131129 | A1 | 5/2016 | Chen | |
| 2017/0343946 | A1* | 11/2017 | Bury | G03G 15/553 |

FOREIGN PATENT DOCUMENTS

| | | |
|---|---|---|
| DE | 102016001806 A1 | 8/2017 |
| GB | 2424928 A | 10/2006 |
| WO | WO 2005/074161 A1 | 8/2005 |
| WO | WO 2005/084354 A2 | 9/2005 |
| WO | WO 2015/094190 A1 | 6/2015 |
| WO | WO 2017/039682 A1 | 3/2017 |

OTHER PUBLICATIONS

United Kingdom Intellectual Property Office, Search Report in United Kingdom Patent Application No. 1804602.9, 1 p. (dated Sep. 21, 2018).

* cited by examiner

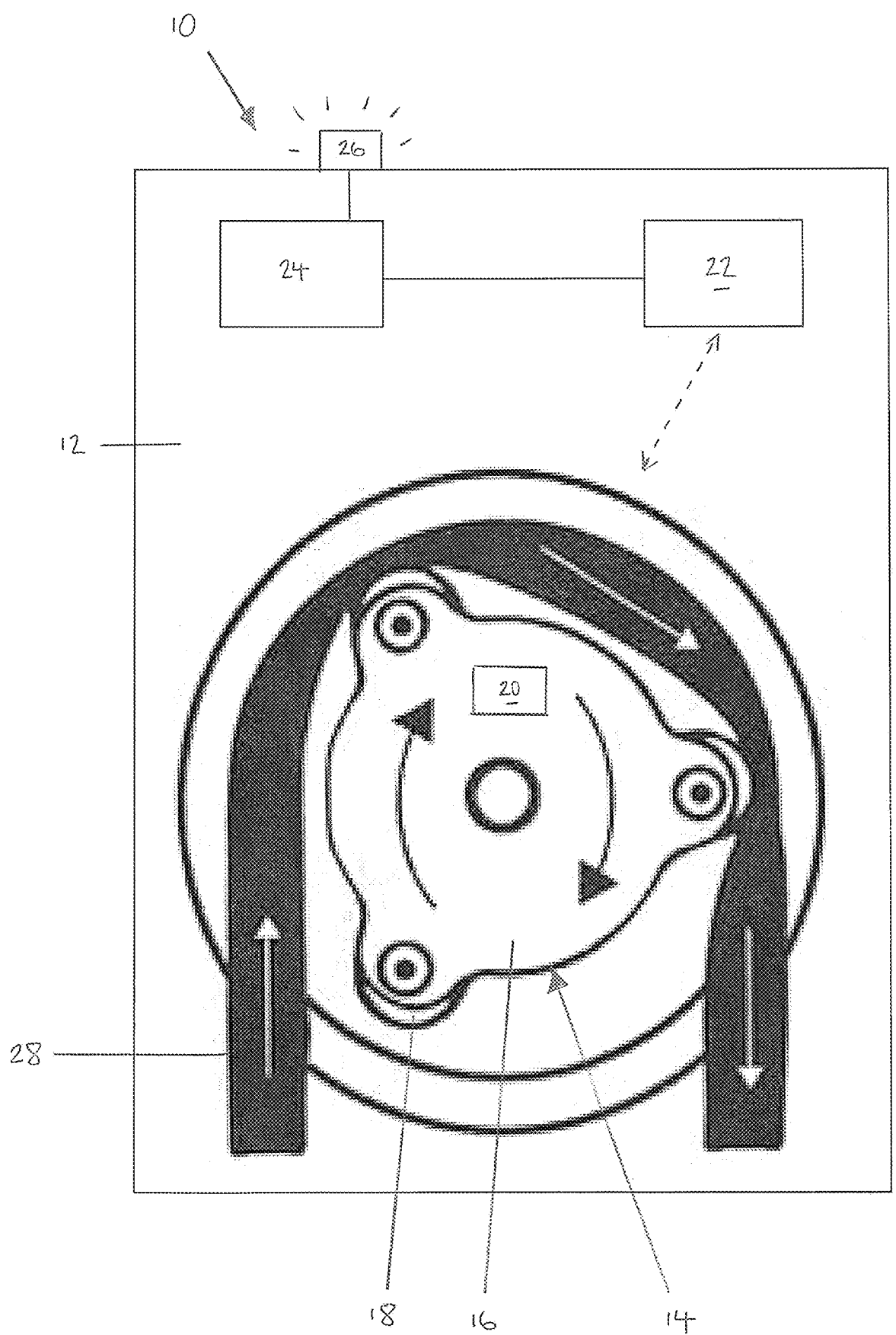

PUMP MONITORING SYSTEM

CROSS-REFERENCE TO RELATED APPLICATIONS

This patent application claims the benefit of U.K. Patent Application No. GB 1804602.9, filed Mar. 22, 2018, which is incorporated by reference.

FIELD OF THE INVENTION

The present invention relates to a pump monitoring system, particularly suitable for a peristaltic pump, which is useful for monitoring usage and wear and for preventive maintenance.

BACKGROUND OF THE INVENTION

Peristaltic pumps are used in many applications, especially in the medical field, where there is a need to maintain pumped fluid in a sterile condition. Typically, a peristaltic pump includes a main pump unit housing a control system, and a rotatable pump head which is removably fitted on the pump unit. The pump head carries rollers which in use compress tubing carrying fluid to be pumped. The pump head will suffer from wear as it is used and must be replaced from time to time to maintain the efficiency of the pump. It is therefore desirable to monitor the wear of the pump head so that a user can be alerted when a replacement is needed, before the wear causes any significant loss of efficiency.

BRIEF SUMMARY OF THE INVENTION

The present invention provides a pump monitoring system, including a pump with a pump body and a pump head releasably fitted to the pump body, an RFID transponder secured to the pump head, and an RFID reader in communication with a processor in the pump body, wherein the RFID transponder is operable to receive and store information relating to operation of the pump head and the RFID reader is operable to read information from the RFID transponder and to transmit further information to the RFID transponder, and the processor is operable to interpret the information read from the transponder and to control operation of the pump in response to the information.

Preferably, the information stored on the RFID transponder includes a unique identifier for the pump head and the number of uses of the pump head.

Preferably, the information further includes a value representing an amount of wear which the pump head has been subjected to.

Preferably, the processor is operable to trigger an alert if either the number of uses or the wear value exceeds a predetermined threshold. The processor may also be operable to trigger an alert if the number of uses or the wear value indicates a pattern of usage outside a predetermined specification for the pump head. Such an alert may be an audible and/or visual warning.

It is also preferable if the pump unit is operable to prevent further operation of the pump head if the number of uses or the wear value exceed a predetermined threshold, or indicate a pattern of use outside a predetermined specification for the pump head.

In a preferred embodiment, the wear value is the product of the duration of pump head operation and the speed of pump head operation.

Preferably, the pump is a peristaltic pump.

The present invention also provides a method of monitoring a pump which includes a pump body and a pump head releasably fitted to the pump body, wherein the method includes providing an RFID transponder secured to the pump head, providing an RFID reader in communication with a processor in the pump body, using the RFID transponder to receive and store information relating to operation of the pump head, using the RFID reader to read information from the RFID transponder and to transmit further information to the RFID transponder as the pump head is operated, and using the processor to interpret the information read from the transponder and to control operation of the pump in response to the information.

Preferably, the information stored on the RFID transponder includes a unique identifier for the pump head and the step of transmitting further information to the RFID transponder includes transmitting the number of uses of the pump head. It may further include transmitting a value representing the amount of wear the pump head has been subjected to.

Preferably, the method further includes the step of triggering an alert if the information stored on the RFID transponder and read by the RFID reader indicates a number of uses or a wear value exceeding a predetermined threshold, or if the information indicates a pattern of usage outside a predetermined specification for the pump head.

The method may also include preventing further operation of the pump head if the information indicates the number of uses or the wear value exceed a predetermined threshold or a pattern of use outside a predetermined specification for the pump head.

BRIEF DESCRIPTION OF THE DRAWING

The invention will now be described in detail, by way of example only, with reference to the accompanying FIG. 1 which is a schematic diagram illustrating a pump in accordance with one embodiment of the present invention.

DETAILED DESCRIPTION OF THE INVENTION

A pump 10 is a peristaltic pump which comprises a main pump unit 12 and a pump head 14. The pump unit 12 is connectable to a power supply and contains a control system and means to drive the pump head 14. The pump head 14 comprises a rotor 16 carrying a plurality of rollers 18. The pump head 14 is releasably attachable to the pump unit 12. The pump unit 12 is operable to rotate the pump head 14 and controls the speed of rotation (e.g. rotations per minute—RPM) and the duration of operation. In use, flexible tubing 28 is fitted around the rotor 16. As the rotor 16 rotates, the rollers 18 compress the tubing 28 to pump fluid through it. These features are conventional for peristaltic pumps.

In accordance with the present invention, the pump 10 includes additional features as follows. An RFID transponder or tag 20 is permanently secured to the pump head 14. The pump unit 12 includes an RFID reader 22 in communication with a processor 24 which is operable to control operation of the pump 10.

The tag 20 is a conventional passive RFID transponder which includes a microchip to store information and an antenna to receive and transmit information. The tag 20 is sufficiently robust that it can be read and have further information written to the microchip and re-read many thousands of times without degrading.

The RFID reader 22 is also a conventional RFID read/write device also including an antenna to receive and transmit information. It is operable to read information stored on the tag 20 and to write further information to the tag 20, as illustrated schematically by the dotted arrow in FIG. 1. The information read from the tag 20 is communicated to the processor 24 which interprets the information and controls operation of the pump 10 in response.

The information stored on the tag 20 includes a unique identifier for the pump head 14. This may be a serial number for the pump head 14. Since the tag 20 is permanently secured to the pump head 14 the unique identifier serves to identify the pump head 14 being used irrespective of which pump unit 12 the pump head 14 is attached to.

The information stored on the tag 20 also includes data representing usage and wear of the pump head 14. Preferably, a usage value is simply a count recorded each time the pump head 14 is operated, i.e. caused to rotate. When the pump head 14 is new and unused the usage value is zero. Each time the pump head 14 is operated this value will increment by one. The usage value increments with every operation of the pump head 14, even if it is only operated for a very short time, because in some medical procedures the pump head 14 may be used multiple times in very short bursts of one second or even less (depending on the reaction time of the user).

In addition to the number of uses, a value representing wear of the pump head 14 is recorded. The life of a pump head 14 is not dependent solely upon the total time for which it has been operated but also the type of use. In some applications, a pump may be run continuously for a period of time and in others it may be operated multiple times in short bursts. These will cause different wear characteristics. Similarly, the speed of rotation affects the amount of wear, so that two pump heads with the same number of uses and total run time may have different wear characteristics if one has been run at twice the speed of the other. Therefore, the wear data is preferably obtained as the product of the time T (i.e. how long the pump head 14 is operated during each use) and the speed S of rotation during each use. Thus, the value recorded for each use is T×S. The wear value is recorded cumulatively so that after each use, the wear value is added to a total obtained from all the previous usages.

The information regarding the number of uses, the run time and the run speed are measured by the processor 24 in the pump unit 12 and the necessary information is communicated to the RFID reader 22 to be written to and subsequently read from the tag 20. The information remains on the tag 20 regardless of which pump unit 12 it is attached to. Information read from the tag 20 is communicated back to the processor 24 to interpret.

If the processor 24 detects a usage value or a wear value greater than a predetermined threshold for the respective value, the processor 24 will operate an alert 26 to the user. This may be a visual alert such as a warning light, and/or an audible alert such as a beeping sound, to notify the use that the pump head 14 should be changed.

In addition, the processor 24 may be operable to prevent further operation of the pump head 14 if the usage value or wear value exceeds a desired threshold, so that the user is forced to change the pump head 14.

It is also possible for the processor 24 to operate an alert and/or cease operation of the pump 10 if the information read from the tag 20 indicates misuse of the pump 14. For example, if it is known that certain profiles of use are outside the specification of a particular pump head 14, e.g. multiple very short uses at maximum speed, this information will be recorded and can be used by the processor 24 to alert the user or stop operation of the pump 10.

Different medical procedures require different patterns of use of a pump 10, leading to different wear characteristics for the pump head 14. For example, a high usage value with a low wear value, indicating multiple uses but for short durations and at low speeds, may occur in procedures such as an endoscope submucosal dissection (ESD). A low usage value with a high wear value, indicating a long run time at high speed, may occur in a gastrointestinal procedure (GI). Therefore, the information collected on the tag 20 will build up a picture of the typical usage of a given pump head and also the type of wear characteristics which can be expected from a pump head generally when it is used in different ways. This information can be used to determine the threshold values employed by the processor 24 to control operation of the pump 10 and whether to trigger the alerts 26.

In this way, the present invention provides a system in which wear of a pump head 14 can be easily monitored and therefore efficiency of a pump 10 can be maintained. It is particularly useful for peristaltic pumps where the pumped fluid is within tubing and does not directly contact any part of the pump, meaning that other methods of monitoring pump efficiency, such as pressure or flow sensors, are difficult or impossible to use. Nevertheless, the present invention may be adapted for use with other types of pump in which certain parts undergo wear due to repeated usage. Accordingly, references to a pump head include parts of a pump which are subject to wear in use and can be replaced to maintain pump efficiency.

The invention claimed is:

1. A pump monitoring system, comprising a pump with a pump body and a pump head releasably mounted on the pump body, an RFID transponder on the pump head, and an RFID reader in communication with a processor on the pump body, wherein the RFID transponder is operable to receive and store information relating to operation of the pump head and the RFID reader is operable to read information from the RFID transponder and to transmit further information to the RFID transponder, and the processor is operable to interpret the information read from the RFID transponder and to control operation of the pump in response to the information, wherein the information stored on the RFID transponder comprises a value representing the amount of wear the pump head has been subjected to and wherein the wear value is the product of the duration of pump head operation and the speed of pump head operation.

2. A pump monitoring system as claimed in claim 1, wherein the information stored on the RFID transponder comprises a unique identifier for the pump head and the number of uses of the pump head.

3. A pump monitoring system as claimed in claim 1, wherein the processor is operable to trigger an alert if the number of uses or the wear value exceeds a predetermined threshold.

4. A pump monitoring system as claimed in claim 1, wherein the processor is operable to trigger an alert if the information indicates a pattern of usage outside a predetermined specification for the pump head.

5. A pump monitoring system as claimed in claim 3, wherein the alert is an audible and/or a visual warning.

6. A pump monitoring system as claimed in claim 3, wherein the processor is operable to prevent further operation of the pump head if the number of uses or the wear value exceed a predetermined threshold, or the information indicates a pattern of use outside a predetermined specification for the pump head.

7. A pump monitoring system as claimed in claim 1, wherein the pump is a peristaltic pump.

8. A method of monitoring a pump comprising a pump body and a pump head releasably mounted on the pump body, the method comprising the steps of providing an RFID transponder on the pump head, providing an RFID reader in communication with a processor in the pump body, using the RFID transponder to receive and store information relating to operation of the pump head, using the RFID reader to read information from the transponder and to transmit further information to the transponder as the pump head is operated, and using the processor to interpret information read from the transponder and to control operation of the pump in response to the information, and wherein the step of transmitting further information to the RFID transponder comprises transmitting a value representing the amount of wear the pump head has been subjected to, and wherein the wear value is the product of the duration of pump head operation and the speed of pump head operation.

9. A method of monitoring a pump as claimed in claim 8, wherein the information stored on the RFID transponder comprises a unique identifier for the pump head and the step of transmitting further information to the RFID transponder comprises transmitting the number of uses of the pump head.

10. A method of monitoring a pump as claimed in claim 7, further comprising the step of triggering an alert if the RFID reader reads information from the RFID transponder indicating that the number of uses or the wear value exceeds a predetermined threshold.

11. A method of monitoring a pump as claimed in claim 8, further comprising the step of triggering an alert if the RFID reader reads information from the RFID transponder which indicates a pattern of usage outside a predetermined specification for the pump head.

12. A method of monitoring a pump as claimed in claim 10, further comprising the step of preventing further operation of the pump head if the information read from the RFID transponder by the RFID reader indicates the number of uses or the wear value exceeds a predetermined threshold, or if the information indicates a pattern of use outside a predetermined specification for the pump head.

* * * * *